United States Patent [19]

Carabateas et al.

[11] B 3,994,903

[45] Nov. 30, 1976

[54] PREPARATION OF 4-(3-NITROPHENYL)PYRIDINE

[75] Inventors: Philip M. Carabateas; Ruth Pauline Brundage, both of Schodack, N.Y.

[73] Assignee: Sterling Drug Inc., New York, N.Y.

[22] Filed: Feb. 25, 1974

[21] Appl. No.: 445,493

[44] Published under the second Trial Voluntary Protest Program on March 2, 1976 as document No. B 445,493.

[52] U.S. Cl. .................. 260/290 R; 260/295 AM; 260/296 R; 260/290 P
[51] Int. Cl.² .................................. C07D 213/26
[58] Field of Search ............ 260/290, 295, 296, 465

[56] References Cited
OTHER PUBLICATIONS

Zollinger, Azo & Diazo Chemistry Aliphatic and Aromatic Compounds, Title page & p. 168, (1961).
Cook et al., J. Chem. Society, (London), pp. 404–406, (1943).

*Primary Examiner*—Harry I. Moatz
*Attorney, Agent, or Firm*—Robert K. Bair; B. Woodrow Wyatt

[57] ABSTRACT

4-(3-nitrophenyl)pyridine, an intermediate useful in the preparation of the antibacterially active 1-alkyl-1,4-dihydro-4-oxo-7-(4-pyridyl)-3-quinolinecarboxylic acids, is prepared by reacting 4-(4-dimethylaminophenyl)pyridine (I) with a demethylating agent to yield 4-(4-aminophenyl)pyridine (II), reacting said 4-aminophenyl compound (II) with a lower-alkanoylating agent to yield 4-[4-(lower-alkanoylamino)-phenyl]pyridine (III), nitrating the 4-(lower-alkanoylamino)-phenyl derivative (III) to yield 4-[4-(lower-alkanoylamino)-3-nitrophenyl]pyridine (IV), hydrolyzing the 4-(lower-alkanoylamino)-3-nitrophenyl compound (IV) to yield 4-(4-amino-3-nitrophenyl)-pyridine (V), and removing the 4-amino group of V by diazotization and reaction of the diazonium salt with a deaminating reducing agent to produce said intermediate 4-(3-nitrophenyl)pyridine (VI). Intermediates IV and V are novel.

9 Claims, No Drawings

PREPARATION OF 4-(3-NITROPHENYL)PYRIDINE

This invention relates to the preparation of 4-(3-nitrophenyl)pyridine and to processes and intermediates used in its preparation.

4-(3-nitrophenyl)pyridine is useful as an intermediate in the preparation of 1-(lower-alkyl)-1,4-dihydro-4-oxo-7-(4-pyridyl)-3-quinolinecarboxylic acids, which are useful as antibacterial agents and which are disclosed and claimed in U.S. Pat. No. 3,753,993, issued Aug. 21, 1973.

The process aspect of the invention resides in the process of producing 4-(3-nitrophenyl)pyridine (VI) which comprises reacting 4-(4-dimethylaminophenyl)-pyridine (I) with a demethylating agent to yield 4-(4-aminophenyl)pyridine (II), reacting said 4-aminophenyl compound (II) with a lower-alkanoylating agent to yield 4-[4-(lower-alkanoylamino)phenyl]pyridine (III), nitrating the 4-(lower-alkanoylamino)phenyl derivative (III) to yield 4-[4-(lower -alkanoylamino)-3-nitrophenyl]pyridine (IV), hydrolyzing the 4-(lower-alkanoylamino)-3-nitrophenyl compound (IV) to yield 4-(4-amino-3-nitrophenyl)pyridine (V), and removing the 4-amino group of V by diazotization and reaction of the diazonium salt with a deaminating reducing agent to produce said intermediate 4-(3-nitrophenyl)pyridine (VI). Other process aspects of the invention reside in each of the first, second, third, fourth and fifth steps of the above described process and sub-combinations thereof.

The overall process of the invention is illustrated structurally by the following chemical formulas:

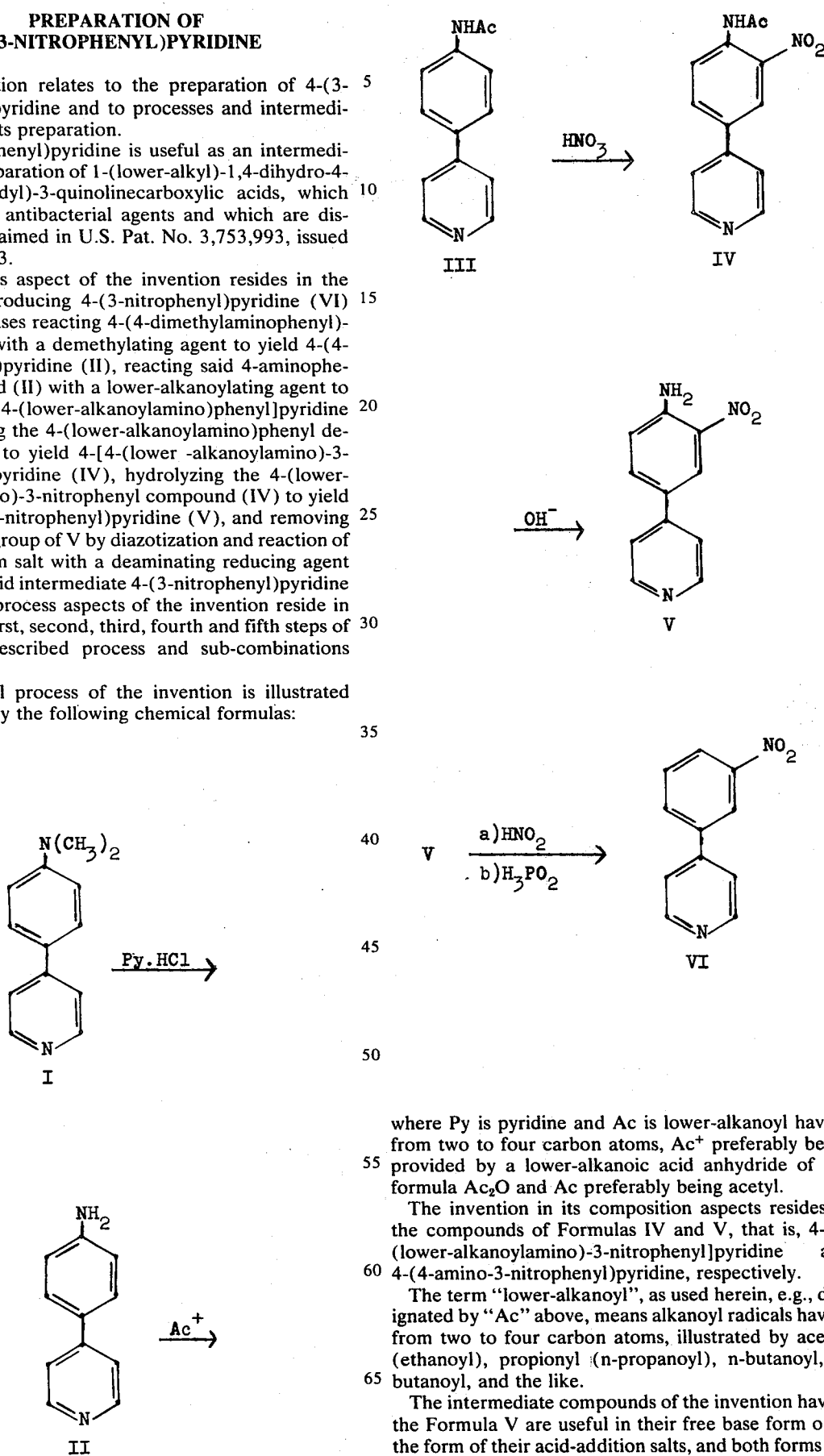

where Py is pyridine and Ac is lower-alkanoyl having from two to four carbon atoms, $Ac^+$ preferably being provided by a lower-alkanoic acid anhydride of the formula $Ac_2O$ and Ac preferably being acetyl.

The invention in its composition aspects resides in the compounds of Formulas IV and V, that is, 4-[4-(lower-alkanoylamino)-3-nitrophenyl]pyridine and 4-(4-amino-3-nitrophenyl)pyridine, respectively.

The term "lower-alkanoyl", as used herein, e.g., designated by "Ac" above, means alkanoyl radicals having from two to four carbon atoms, illustrated by acetyl, (ethanoyl), propionyl (n-propanoyl), n-butanoyl, 2-butanoyl, and the like.

The intermediate compounds of the invention having the Formula V are useful in their free base form or in the form of their acid-addition salts, and both forms are within the purview of the invention, and are considered to be one and the same invention. The acid-addition salts are simply a more convenient form for use; and, in practice, use of the salt form inherently amounts to use of the base form. In practicing our invention, we found it convenient to employ the hydrochloride salt. However, other appropriately acceptable salts within the scope of the invention are those derived from mineral acids, such as hydrobromic acid, hydriodic acid, nitric acid, phosphoric acid, sulfamic acid and sulfuric acid; and organic acids such as acetic acid, tartaric acid, methanesulfonic acid, ethanesulfonic acid, benzenesulfonic acid, and the like, giving the hydrobromide, hydriodide, nitrate, phosphate, sulfamate, sulfate, acetate, tartrate, methanesulfonate, ethanesulfonate and benzenesulfonate, respectively. Preferred salts are pharmaceutically acceptable acid-addition salts.

The acid-addition salts are prepared preferably by reacting the free base and acid in an organic solvent, e.g., ethanol, acetone, etc., in which the salt separates directly or can be obtained by concentration of the solution.

The molecular structures of said composition aspects of the invention were assigned on the basis of evidence provided by infrared, ultraviolet and nuclear magnetic resonance spectra, by chromatographic mobilities, and by the correspondence of calculated and found values for the elementary analysis for representative examples.

The manner of making and using the instant invention will now be generally described so as to enable a person skilled in the art of pharmaceutical chemistry to make and use the same, as follows:

The known 4-(4-dimethylaminophenyl)pyridine is readily prepared by published procedures, e.g., by first heating a mixture of pyridine and benzoyl chloride in the presence of copper powder and then heating the resulting mixture with N,N-dimethylaniline [Koenigs et al., Ann. 509, 142 (1934)].

The reaction of 4-(4-dimethylaminophenyl)pyridine (I) with a demethylating agent to yield 4-(4-aminophenyl)pyridine (II) is carried out by heating the reactants, preferably using pyridine hydrochloride or hydrobromide as the demethylating agent, at about 130°–260°C., preferably about 210°–230°C. The reaction is conveniently run using pyridine and concentrated hydrochloric acid.

The reaction of 4-(4-aminophenyl)pyridine (II) with a lower-alkanoylating agent to yield 4-[4-(lower-alkanoylamino)phenyl]pyridine (III) is carried out preferably using a lower-alkanoic acid anhydride, preferably acetic anhydride, and heating the reactants at about 50°–150°C., preferably at about 90°–110°C. Alternatively, the reaction can be run using, in place of said acid anhydride, other lower-alkanoylating agents, e.g., a lower-alkanoyl halide preferably at about −5° to 10°C. in the presence of an acid-acceptor, e.g., an alkali hydroxide or an alkali carbonate or bicarbonate, by stirring in a medium comprising water and a suitable water-immiscible organic solvent inert under the reaction conditions, e.g., ethylene dichloride, chloroform, methylene dichloride, ether, benzene, and the like.

The nitration of 4-[4-(lower-alkanoylamino)phenyl]pyridine (III) to yield 4-[4-(lower-alkanoylamino)-3-nitrophenyl]pyridine (IV) is carried out by reacting III with concentrated nitric acid (90%) at a low temperature, preferably keeping the reaction temperature below 0°C.

The hydrolysis of 4-[(lower-alkanoylamino)-3-nitrophenyl]pyridine (IV) to yield 4-(4-amino-3-nitrophenyl)pyridine (V) is readily carried out by heating IV at about 50°–150°C., preferably about 90°–110°C., in aqueous alkali hydroxide solution, preferably sodium or potassium hydroxide solution.

The conversion of 4-(4-amino-3-nitrophenyl)pyridine (V) to 4-(3-nitrophenyl)pyridine (VI) is conveniently run by diazotizing the 4-amino group [by reaction of (V) with nitrous acid, in aqueous acidic medium preferably using a mineral acid, e.g., hydrochloric acid, and an alkali nitrite, e.g., sodium nitrate] at about −5° to 5°C. and then treating the cold solution of resulting diazonium salt with a deaminating reducing agent, preferably cold hypophosphorous acid or an alkali hypophosphite at about −5° to 5°C. Other deaminating reducing agents can be used in place of the preferred hypophosphorous acid. Thus, sodium borohydride can be used in reducing the corresponding diazonium borofluoride in nonaqueous media, e.g., solid sodium borohydride is added to a chilled methanolic solution or suspension of said diazonium borofluoride or a chilled solution of sodium borofluoride in dimethylformamide is added to a chilled solution of said diazonium borofluoride in dimethylformamide. Also, the reductive deamination can be run using the diazonium hexafluorophosphate as the diazonium salt and tetramethylurea as the deaminating reducing agent, the reduction being carried out preferably by reacting the two reactants at about 25° to 65°C.

The best mode contemplated for carrying out the invention is now set forth as follows:

1. 4-(4-aminophenyl)pyridine

To a mixture containing 143.2 g. of 4-(4-dimethylaminophenyl)pyridine and 1000 ml. of concentrated hydrochloric acid was added 800 ml. of pyridine. The reaction mixture was then heated, first to distill off the water, and then it was refluxed under an air condenser for 3 hours, the reaction temperature being between 210°–225°C. The reaction mixture was poured onto ice; the mixture was made alkaline with 35% aqueous sodium hydroxide solution; and, the alkaline mixture was diluted with water to a total volume of about five liters. The resulting solid was collected, dissolved in 400 ml. of boiling dimethylformamide and the solution filtered. The hot solution was diluted with 1500 ml. of hot acetonitrile. The tan crystalline precipitate was collected and air-dried to yield 75 g. of 4-(4-aminophenyl)pyridine, m.p. 232°–234°C.

2. 4-(4-acetamidophenyl)pyridine

To 1400 ml. of acetic anhydride was added with stirring 163.7 g. of 4-(4-aminophenyl)pyridine and the resulting reaction mixture was heated with stirring on a steam bath for 1 hour. The reaction mixture was cooled; the solid that separated was collected, washed with ether and air-dried to yield 147 g. of 4-(4-acetamidophenyl)pyridine, m.p. 200°–215°C.

In another run using 10 g. of 4-(4-aminophenyl)pyridine and 300 ml. of acetic anhydride, there was obtained 10.8 g. of 4-(4-acetamidophenyl)pyridine, m.p. 209°–211°C. after washing with n-hexane and drying in vacuo at 50°C.

3. 4-(4-acetamido-3-nitrophenyl)pyridine

To 160 ml. of nitric acid (90%) cooled to less than 0°C. in an ice-ethanol bath was slowly added with stirring 42 g. of 4-(4-acetamidophenyl)pyridine over a period of about twenty minutes. The reaction mixture was then stirred for 45 minutes, keeping the reaction temperature below 0°C. The reaction mixture was then poured onto ice and the mixture treated with 35% aqueous sodium hydroxide solution, adding ice to keep the mixture cool. The resulting yellow solid was collected, washed with water and air-dried to yield 43.7 g. of 4-(4-acetamido-3-nitrophenyl)pyridine, which was used directly in Example 4 without further purification.

4. 4-(4-amino-3-nitrophenyl)pyridine

A mixture containing 43.7 g. of 4-(4-acetamido-3-nitrophenyl)pyridine, 175 ml. of 2N potassium hydroxide solution and enough water to bring the total volume to 1 liter was heated with stirring on a steam bath for 3 hours. After the reaction mixture had cooled to room temperature, the resulting yellow solid was collected, washed successively with water and a small volume of ethanol, air-dried and recrystallized from dimethylformamide to yield 21.6 g. of 4-(4-amino-3-nitrophenyl)pyridine, m.p. 234°–237.5°C.

5. 4-(3-nitrophenyl)pyridine

A mixture containing 10.0 g. of 4-(4-amino-3-nitrophenyl)pyridine, 20 ml. of concentrated hydrochloric acid and 80 ml. of water was cooled to 0°C. with stirring. To the cold solution was added dropwise with stirring and cooling a solution containing 3.7 g. of sodium nitrite in 20 ml. of water over a 15 minute period, keeping the reaction temperature below 5°C. The reaction mixture was stirred for an additional 15 minutes at the same temperature. To the cold solution kept at about 0°C. was added 25 ml. of cold hypophosphorous acid (50%); the mixture was stirred at 0°C. for 3 hours and then allowed to stand in a refrigerator over the weekend (two days). The reaction mixture was made alkaline with concentrated ammonium hydroxide and the product was extracted with chloroform. The chloroform solution was dried over anhydrous magnesium sulfate, treated with decolorizing charcoal and filtered. The filtrate was evaporated to dryness and the resulting tan solid residue was recrystallized from isopropyl acetate to yield 6.3 g. of 4-(3-nitrophenyl)pyridine, m.p. 110°–113°C.

Utilization of 4-(3-nitrophenyl)pyridine in the preparation of the above-noted antibacterially active 1-(lower-alkyl)-1,4-dihydro-4-oxo-7-(4-pyridyl)-3-quinolinecarboxylic acids is illustrated in said U.S. Patent No. 3,753,993, e.g., Examples 1B, 1C, 1D and 1A thereof.

We claim:

1. The process which comprises reacting 4-(4-dimethylaminophenyl)pyridine with pyridine hydrochloride or hydrobromide at about 130°–260°C. to yield 4-(4-aminophenyl)pyridine, reacting said 4-aminophenyl compound with a lower-alkanoylating agent selected from lower-alkanoic anhydride or lower-alkanoyl halide the latter in the presence of alkali hydroxide, carbonate or bicarbonate to yield 4-[4-(lower-alkanoylamino)phenyl]pyridine, reacting the 4-(lower-alkanoylamino)phenyl derivative with concentrated nitric acid below 0°C. to yield 4-[4-(lower-alkanoylamino)-3-nitrophenyl]pyridine, reacting the 4-(lower-alkanoylamino)-3-nitrophenyl compound with aqueous alkali hydroxide solution at about 50°–150°C. to yield 4-(4-amino-3-nitrophenyl)pyridine, and removing the 4-amino group by diazotization of 4-(4-amino-3-nitrophenyl)pyridine as its mineral acid addition salt and reaction of the diazonium salt with a deaminating reducing agent selected from hypophosphorous acid, sodium borohydride and tetramethylurea to produce 4-(3-nitrophenyl)pyridine.

2. The process according to claim 1 where lower-alkanoyl is acetyl.

3. The process according to claim 1 where the lower-alkanoylating agent is acetic anhydride.

4. In the process according to claim 1, the step which comprises reacting 4-(4-dimethylaminophenyl)pyridine with pyridine hydrochloride or hydrobromide at about 130°–260°C. to yield 4-(4-aminophenyl)pyridine.

5. In the process according to claim 1, the step which comprises removing the 4-amino group of 4-(4-amino-3-nitrophenyl)pyridine by diazotization of 4-(4-amino-3-nitrophenyl)pyridine as its mineral acid addition salt and reaction of the diazonium salt with a deaminating reducing agent selected from hypophosphorous acid, sodium borohydride and tetramethylurea to produce 4-(3-nitrophenyl)pyridine.

6. The process according to claim 5 where the deaminating reducing agent is hypophosphorous acid.

7. In the process according to claim 1 the steps which comprise reacting 4-(4-aminophenyl)pyridine with a lower-alkanoylating agent selected from lower-alkanoic anhydride or lower-alkanoyl halide the latter in the presence of alkali hydroxide, carbonate or bicarbonate to yield 4-[4-(lower-alkanoylamino)phenyl]pyridine, reacting 4-[4-(lower-alkanoylamino)phenyl]pyridine with concentrated nitric acid below 0°C. to yield 4-[4-(lower-alkanoylamino)-3-nitrophenyl]pyridine, reacting 4-[4-(lower-alkanoylamino)-3-nitrophenyl]pyridine with aqueous alkali hydroxide solution at about 50°–150°C. to yield 4-(4-amino-3-nitrophenyl)pyridine, and removing the 4-amino group of 4-(4-amino-3-nitrophenyl)pyridine by diazotization of 4-(4-amino-3-nitrophenyl)pyridine as its mineral acid addition salt and reaction of the diazonium salt with a deaminating reducing agent selected from hypophosphorous acid, sodium borohydride and tetramethylurea to produce 4-(3-nitrophenyl)pyridine.

8. In the process according to claim 1, the steps which comprise reacting 4-[4-(lower-alkanoylamino)phenyl]pyridine with concentrated nitric acid below 0°C. to yield 4-[4-(lower-alkanoylamino)-3-nitrophenyl]pyridine, reacting 4-[4-(lower-alkanoylamino)-3-nitrophenyl]pyridine with aqueous alkali hydroxide solution at about 50°–150°C. to yeild 4-(4-amino-3-nitrophenyl)pyridine, and removing the 4-amino group of 4-(4-amino-3-nitrophenyl)pyridine by diazotization of 4-(4-amino-3-nitrophenyl)pyridine as its mineral acid addition salt and reaction of the diazonium salt with a deaminating reducing agent selected from hypophosphorous acid, sodium borohydride and tetramethylurea to produce 4-(3-nitrophenyl)pyridine.

9. In the process according to claim 1, the steps which comprise reacting 4-[4-(lower-alkanoylamino)-3-nitrophenyl]pyridine with aqueous alkali hydroxide solution at about 50°–150°C. to yield 4-(4-amino-3-nitrophenyl)pyridine and removing the 4-amino group of 4-(4-amino-3-nitrophenyl)pyridine by diazotization of 4-(4-amino-3-nitrophenyl)pyridine as its mineral acid addition salt and reaction of the diazonium salt with a deaminating reducing agent selected from hypophosphorous acid, sodium borohydride and tetramethylurea to produce 4-(3-nitrophenyl)pyridine.

* * * * *